US011094424B2

(12) United States Patent
Franci et al.

(10) Patent No.: US 11,094,424 B2
(45) Date of Patent: Aug. 17, 2021

(54) CLOSED EVAPORATION SYSTEM

(71) Applicant: GE HEALTHCARE LIMITED, Buckinghamshire (GB)

(72) Inventors: Xavier Franci, Loncin (BE); Steve Lignon, Loncin (BE); Audrey Lange, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 16/555,484

(22) Filed: Aug. 29, 2019

(65) Prior Publication Data

US 2020/0043620 A1 Feb. 6, 2020

Related U.S. Application Data

(63) Continuation of application No. 15/027,633, filed as application No. PCT/EP2014/072302 on Oct. 17, 2014, now abandoned.

(30) Foreign Application Priority Data

Oct. 18, 2013 (GB) ..................................... 1318450

(51) Int. Cl.
| | |
|---|---|
| *A61K 51/00* | (2006.01) |
| *A61M 36/14* | (2006.01) |
| *G21F 9/08* | (2006.01) |
| *G21G 4/08* | (2006.01) |
| *C07H 19/06* | (2006.01) |
| *B01J 19/00* | (2006.01) |
| *C07B 59/00* | (2006.01) |
| *C07C 227/40* | (2006.01) |
| *C07D 233/91* | (2006.01) |
| *C07J 1/00* | (2006.01) |
| *G21G 1/00* | (2006.01) |
| *B01D 1/30* | (2006.01) |

(52) U.S. Cl.
CPC ................. *G21F 9/08* (2013.01); *B01D 1/30* (2013.01); *B01J 19/0093* (2013.01); *C07B 59/00* (2013.01); *C07B 59/005* (2013.01); *C07C 227/40* (2013.01); *C07D 233/91* (2013.01); *C07H 19/06* (2013.01); *C07J 1/007* (2013.01); *G21G 1/0005* (2013.01); *G21G 4/08* (2013.01); *B01J 2219/009* (2013.01); *B01J 2219/00799* (2013.01); *B01J 2219/00873* (2013.01); *B01J 2219/00885* (2013.01); *B01J 2219/00959* (2013.01); *B01J 2219/00963* (2013.01); *C07B 2200/05* (2013.01); *C07C 2601/04* (2017.05)

(58) Field of Classification Search
USPC ....................................................... 424/1.89
See application file for complete search history.

(56) References Cited

U.S. PATENT DOCUMENTS

| | | | |
|---|---|---|---|
| 3,292,151 A | 12/1966 | Barnes et al. | |
| 3,293,151 A | 12/1966 | Holzer et al. | |
| 2009/0312564 A1 | 12/2009 | Arstad | |
| 2013/0209358 A1* | 8/2013 | Barnett | A61K 51/088 424/1.69 |

FOREIGN PATENT DOCUMENTS

| | | |
|---|---|---|
| GB | 1163099 A | 9/1969 |
| JP | H0552995 A | 2/1993 |
| JP | H0552995 | 3/1993 |
| KR | 1020130005917 A | 1/2013 |
| RU | 2477538 C1 | 3/2013 |
| WO | 2008101305 A1 | 8/2008 |
| WO | 2012170602 A1 | 12/2012 |
| WO | 2013079578 A1 | 6/2013 |

OTHER PUBLICATIONS

Atkins Physical Chemistry 1999, 89.
Russia Office Action and Search Report corresponding to Russian Application No. 2016112554/07, dated Jun. 14, 2018, 15 pages (6 pages of English Translation + 9 pages Official Copy).
International Search Report and Written Opinion corresponding to International Application No. PCT/EP2014/0723032, dated Mar. 2, 2015, 10 pages.
Search Report regarding Great Britain Application No. 1318450.2, dated Jul. 16, 2014, 3 pages.
Korean Preliminary Rejection received in Application No. 10-2016-7009628 dated Oct. 13, 2020, 13 pages.

* cited by examiner

*Primary Examiner* — Michael G. Hartley
*Assistant Examiner* — Sean R Donohue
(74) *Attorney, Agent, or Firm* — Jeff B. Vockrodt; Culhane Meadows, PLLC

(57) ABSTRACT

The present invention provides a system for evaporating a radioactive fluid, a method for the synthesis of a radiolabelled compound including this system, and a cassette for the synthesis of a radiolabelled compound comprising this system. The present invention provides advantages over known methods for evaporation of a radioactive fluid as it reduces drastically the amount of radioactive gaseous chemicals that are released in the hot cell. It is gentler and more secure compared to the known process and provides access to radiosyntheic processes that may not been acceptable for safety reasons related to release of volatile radioactive gases during evaporation. In addition, the process yields are higher because the radioactive volatiles are labelled intermediate species.

20 Claims, 3 Drawing Sheets

CLOSED EVAPORATION SYSTEM

CROSS-REFERENCE TO RELATED APPLICATIONS

This application is a continuation U.S. application Ser. No. 15/027,633, dated Apr. 6, 2016, which is a filing under 35 U.S.C. 371 of international application number PCT/EP2014/072302, filed Oct. 17, 2014, which claims priority to application number 1318450.2 filed in Great Britain on Oct. 18, 2013, the entire disclosures of each of which are hereby incorporated by reference.

TECHNICAL FIELD OF THE INVENTION

The present invention relates to the field of radiolabelled compounds and in particular to their preparation. More specifically, the present invention relates to systems and methods for evaporation of a radioactive fluid.

DESCRIPTION OF RELATED ART

Evaporation or drying processes typically include an evaporation chamber submitted to a certain temperature under a reduced pressure and connected to a vacuum pump. A slight inert gas flow, e.g. nitrogen flow, can be applied in order to ease the evaporation of the solvent. Such processes are well-known to the person skilled in the art.

The system illustrated in FIGS. 1A and 1B illustrate a known process for evaporation. The system includes a heating means 1 for a container of radioactive fluid 2 (as shown in FIG. 1A) wherein evaporation or drying (as shown in FIG. 1B) of the radioactive fluid 2 is effected by heating in conjunction with application of a vacuum. Such a system is extremely efficient when there is no potential radioactive gaseous material that can be extracted from the solution to be evaporated. Radioactive gaseous material is released through the vacuum pump into the hot cell or a chimney in the hot cell, and this radioactive gaseous release is subject to measurement and regulatory limits. These limits are becoming progressively lower with time. Therefore there is a need for an evaporation system that limits the gaseous radioactive release as low as possible.

SUMMARY OF THE INVENTION

The present invention provides a system for evaporating a radioactive fluid, a method for the synthesis of a radiolabelled compound including this system, and a cassette for the synthesis of a radiolabelled compound comprising this system. The present invention provides advantages over known methods for evaporation of a radioactive fluid as it reduces drastically the amount of radioactive gaseous chemicals that are released in the hot cell. It is gentler and more secure compared to the known process and provides access to radiosyntheic processes that may not be acceptable for safety reasons related to release of volatile radioactive gases during evaporation. In addition, the process yields are higher because the radioactive volatiles are labelled intermediate species.

DETAILED DESCRIPTION OF THE PREFERRED EMBODIMENTS

In one aspect the present invention provides a system for evaporating a radioactive fluid wherein said system comprises:

(i) a fixed volume hot zone which comprises a fixed volume container and a heating means;
(ii) an expandable volume;
(iv) a 3-way valve which in a first position fluidly connects said fixed volume container and said an expandable volume and which in a second position fluidly connects said an expandable volume to waste.

The "fixed volume hot zone" is essentially an evaporation chamber having a fixed volume heated using any one of a variety of well-known suitable means, e.g. a conductive material mantle. This fixed volume hot zone is connected to the "expandable volume", which is a condensation chamber that has a variable volume, e.g. a syringe, which is in a colder, unheated, area.

The "3-way valve" is any valve that permits selection between (i) fluid connection of the fixed volume hot zone to the expandable volume and (ii) fluid connection between the expandable volume and waste. An example of a suitable such valve is a T-shaped ball valve.

All elements of the system of the invention should be made from radiostable materials, and at least stable in the presence of the particular radioactive isotope being used in the system.

The principle of the present invention is that the solution to be evaporated is heated above its boiling point in order to reach the equilibrium gas/liquid phase. A variable volume is connected to the system and the expansion of the volume displaces the equilibrium in favour of the gaseous phase. As the variable volume is in a cold area, the vapours condense in it. A 3-way valve allows the condensed vapours in the variable volume to be emptied to waste and then reconnected to the evaporation chamber. This operation can be repeated several times until the desired dryness is obtained.

It is intended that system of the invention is used within the confines of a hot cell due to the radioactive nature of the operations carried out with it. As compared with known processes, a reduced amount of radioactive volatiles is released into the hot cell and/or via the hot cell chimney.

FIGS. 2A and 2B illustrate an exemplary system of the present invention and a method for its use. A volume of radioactive fluid 12 is contained within a fixed volume hot zone 11 which comprises a fixed volume container 11a and heating means 11b. The fixed volume container 11a is fluidly connected via a 3-way valve 15 to an expandable volume, which as illustrated in FIGS. 2A and 2B is a syringe 13. Heating of the radioactive fluid 12 in the fixed volume container 11a above its boiling point causes it to vaporise and move into syringe 13 when valve 15 is in a first position. The plunger of syringe 13 becomes displaced by the movement of vaporised radioactive fluid from the fixed volume container 11a. When the vaporised radioactive fluid enters the syringe 13 it condenses due to the drop in temperature to form a volume of radioactive fluid 14 in the syringe. When the syringe 13 is full the radioactive fluid 14 can be sent to waste by moving valve 15 into a second position and pushing down the plunger of the syringe 13 as shown in FIG. 2B. Once syringe 13 is empty the process can be repeated to evaporate further radioactive fluid 12 from the fixed volume hot zone.

In one embodiment of the system of the invention the fixed volume container of the system of the invention is a reaction vessel, i.e. the vessel in which the radiolabelling reaction is carried out.

In one embodiment of the system of the invention the expandable volume of the system of the invention is a syringe.

In another aspect the present invention provides a method for the synthesis of a radiolabelled compound wherein said method comprises:

(i) radiolabelling a protected precursor compound to obtain a protected radiolabelled compound;

(ii) deprotecting the protected radiolabelled compound obtained from radiolabelleing step (i) to obtain said radiolabelled compound wherein said deprotection is effected using a hydrolysis medium; and, (iii) evaporating the hydrolysis medium following deprotection step (ii) wherein said evaporating is carried out using the system as defined hereinabove.

The term "radiolabelled compound" refers to a compound that comprises a radioactive atom.

The term "radiolabelling" refers to the radiochemical process by which a radioactive atom is incorporated into a non-radioactive compound to obtain a radiolabelled compound.

The term "precursor compound" refers to a non-radioactive compound a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity.

The term "protected" refers to wherein one or more protecting groups are included in a chemical compound in order to direct chemical reaction to a particular site on that compound. By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described by Theorodora W. Greene and Peter G. M. Wuts in "Protective Groups in Organic Synthesis" (Fourth Edition, John Wiley & Sons, 2007).

The term "protected radiolabelled compound" refers to a radiolabelled compound comprising protecting groups.

The term "deprotecting" refers to the process of removing any protecting groups form a protected chemical compound. Deprotection is typically carried out using processes well-known to the skilled person (as described in Greene and Wuts, supra), e.g. by hydrolysis using an acidic or an alkaline solution. A "hydrolysis medium" is a solution suitable for effecting deprotection and is typically an acidic or an alkaline solution.

For said evaporating step, the identically-named embodiments described hereinabove for the system of the invention are equally applicable.

In one embodiment of the method of the invention said radiolabelled compound is a radiopharmaceutical. The term "radiopharmaceutical" refers to a radiolabelled compound suitable for use in a diagnostic or therapeutic method. There are many radiopharmaceuticals well-known to those of skill in the art. Of particular interest in the context of the present invention are radiopharmaceuticals that are diagnostic radiopharmaceuticals. The reader is directed to "Handbook of radiopharmaceuticals: radiochemistry and applications" (Wiley 2003; Welch and Redvanly, Eds.) for more detail.

In one embodiment of the method of the invention said radiolabelled compound is a diagnostic radiopharmaceutical that is either a single photon emission tomography (SPECT) tracer or a positron emission tomography (PET) tracer. There are a variety of well-known SPECT and PET tracers wherein at least one method for their preparation involves an evaporation step and would therefore benefit from the present invention. The reader is referred to "Molecular Imaging: Radiopharmaceuticals for PET and SPECT" (Springer-Verlang 2009; Vallabhajosula, Ed.) for more detail.

PET tracers are of particular interest, especially those that are [11C]-labelled or [18F]-labelled. A number of PET tracers are well known in the art and the reader is referred in this regard to Chapter 6 of "Basic Sciences of Molecular Medicine" (Springer-Verlang 2011; Khalil, Ed.) and to Chapter 8 of "Basics of PET Imaging: Physics, Chemistry and Regulations" (Springer 2010; Saha, Ed.).

In one embodiment of the method of the present invention the radiolabelled compound is an [18F]-labelled PET tracer. Non-limiting examples of such [18F]-labelled PET tracers include [18F]fluorodeoxyglucose ([18F]FDG), [18F]fluorothymidine ([18F]FLT), anti-1-amino-3-[18F]fluorocyclobutyl-1-carboxylic acid ([18F]FACBC), [18F]fluoromisonidazole ([18F]FMISO), [18F]fluoro-L-DOPA ([18F]DOPA), O-(-2-[18F]fluoroethyl)-L-tyrosine ([18F]FET), 16α-[18F]fluoro-17β-estradiol ([18F]FES) and [18F]-1-(5-fluoro-5-deoxy-α-aribinofuranosyl)-2-nitroimidazole ([18F]-FAZA). [18F]FDG, [18F]FLT, [18F]FACBC and [18F]FMISO are of particular interest.

To demonstrate the advantages of the present invention, it has been applied to the synthesis of [18F]FLT. Since the method of the invention is not concerned with the radiochemistry for any particular tracer, these advantages would also be reasonably expected if the method of the invention were to be applied to any radiosynthetic process comprising an evaporation step.

[18F]FLT may be synthesized from a protected precursor compound such as 5'-O-(4',4'-dimethoxytrityl) thymidine by nucleophilic substitution (with inversion of stereo chemistry) at the 3' position using [18F] as illustrated in Scheme 1:

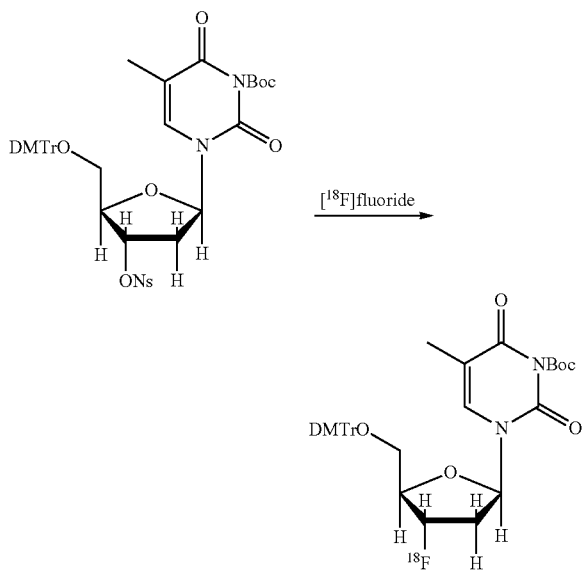

In Scheme 1 DMTr is dimethoxytrityl, Ns is nosyl, and Boc is t-butyloxycarbonyl. The protected precursor compound is labelled with [18F] using [18F]fluoride, which displaces the nosyl leaving group. An exemplary method is described by Grierson and Shields (2000 Nuc Med Biol; 27(2): 143-56). Following radiofluorination the protecting groups can be removed by hydrolysis, e.g. using a hydrolysis medium comprising acetonitrile/water/$H_3PO_4$. The hydrolysis medium is evaporated following hydrolysis. This evaporation under classical method conditions generates radioactive volatiles that end up in the hot cell. In experiments carried out by the present inventors it has been demonstrated that the activity balance shows an activity loss of 10 to 15% in classical conditions, where the closed evaporation system show a loss of activity lower than 5%. The present inventors believe that this effect is not tracer-dependent and anticipates that a similar advantage would be obtainable for any radioactive compound prepared under similar conditions, and in particular the [$^{18}$F]-labelled PET tracers mentioned herein.

In one embodiment, the method of the invention is automated. [$^{18}$F]-labelled PET tracers in particular are often now prepared in an automated fashion by means of an automated radiosynthesis apparatus. By the term "automated synthesis apparatus" is meant an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Such automated synthesis apparatuses are preferred for the method of the present invention especially when a radiopharmaceutical composition is desired. Automated synthesis apparatuses are commercially available from a range of suppliers including: GE Healthcare (Chalfont St Giles, UK); CTI Inc (Knoxville, USA); Ion Beam Applications S.A. (Chemin du Cyclotron 3, B-1348 Louvain-La-Neuve, Belgium); Raytest (Germany) and Bioscan (USA).

A commercial automated synthesis apparatus provides suitable containers for the liquid radioactive waste generated as a result of the radiopharmaceutical preparation. Automated synthesis apparatuses are not typically provided with radiation shielding, since they are designed to be employed in a suitably configured radioactive work cell (also referred to herein as a "hot cell"). The radioactive work cell provides suitable radiation shielding to protect the operator from potential radiation dose, as well as ventilation to remove chemical and/or radioactive vapours. With the present invention the amount of radioactive vapours to be removed is reduced. The automated synthesis apparatus preferably carries out the radiosynthesis by means of a cassette. By the term "cassette" is meant a piece of apparatus designed to fit removably and interchangeably onto an automated synthesis apparatus, in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesis apparatus. External rotation of the arm thus controls the opening or closing of the valve when the cassette is attached to the automated synthesis apparatus. Additional moving parts of the automated synthesis apparatus are designed to clip onto syringe plunger tips, and thus raise or depress syringe barrels. The cassette is versatile, typically having several positions where reagents can be attached, and several suitable for attachment of syringe vials of reagents or chromatography cartridges (e.g. for SPE). The cassette always comprises a reaction vessel. Such reaction vessels are preferably 0.5 to 10 mL, more preferably 0.5 to 5 mL and most preferably 0.5 to 4 mL in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and also resistant to radiolysis.

A disposable or single use cassette comprises all the reagents, reaction vessels and apparatus necessary to carry out the preparation of a given radiopharmaceutical. The cassette means that the automated synthesis apparatus has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In yet another aspect the present invention provides a cassette for the synthesis of a radiopharmaceutical wherein said cassette comprises:
(i) a vessel containing a protected precursor compound;
(ii) means for eluting the vessel of step (i) with a suitable source of a radiolabel; and,
(iii) the system of the invention as defined hereinabove.

The term "cassette" is as defined hereinabove.

The term "radiopharmaceutical" is as defined hereinabove.

The term "protected precursor compound" is as defined hereinabove.

The term "suitable source of a radiolabel" refers to the radiolabel in a form suitable for chemical reaction with the protected precursor compound leading to the formation of the corresponding protected radiolabelled compound. For example, when the radiolabel is $^{18}$F one suitable form is [$^{18}$F]fluoride ion ($^{18}$F$^-$) obtained as an aqueous solution from the nuclear reaction $^{18}$O (p,n)$^{18}$F and typically made reactive by the addition of a cationic counterion and the subsequent removal of water. This form of $^{18}$F$^-$ can displace a leaving group in the protected precursor compound to form an $^{18}$F-labelled protected precursor compound.

The present inventors have demonstrated herein that using the system of the present invention as part of the FASTlab™ manufacture of [$^{18}$F]FLT results in a reduction in losses of radioactivity to less than 5%.

FIGS. 3A and 3B illustrate a FASTlab™ cassette suitable for the synthesis of [$^{18}$F]FLT. The cassette comprises the system of the invention for evaporation of radioactive fluid. FIG. 3A shows a fixed volume hot zone which is a COC reaction vessel 21, a 6 ml syringe 23, a tube connection 26 between the reaction vessel 21 and the syringe 23, 3-way valve 25 that connects the reaction vessel 21 to either the syringe 23 or a waste container. FIG. 3B shows the same elements as FIG. 3A except that the plunger of syringe 23 is raised as it would be when radioactive fluid passes into it from the reaction vessel 21.

The drying process of the invention is gentler and more secure compared to the known process. Due to the volatiles condensing in the colder part of the system, the system of the invention reduces drastically the amount of radioactive gaseous chemicals that are released in the hot cell. The gaseous radioactive material release during a PET tracer synthesis can be problematic and acceptable limits are becoming more and more stringent. The evaporation system of the invention will give access to processes that may not been acceptable for safety reasons related to release of volatile radioactive gases during evaporation. On top of the safety concerns, the overall process yields are higher as well because the radioactive volatiles are labelled intermediate species.

BRIEF DESCRIPTION OF THE EXAMPLES

Figure 1A:
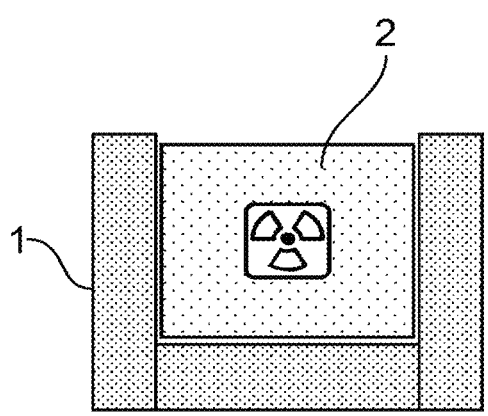
FIGS. 1A and 1B illustrate a known process for evaporation or drying.
Figure 1B:
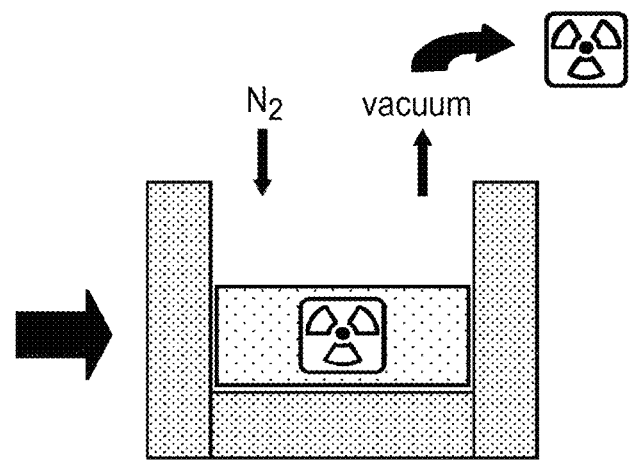
Figure 2A:
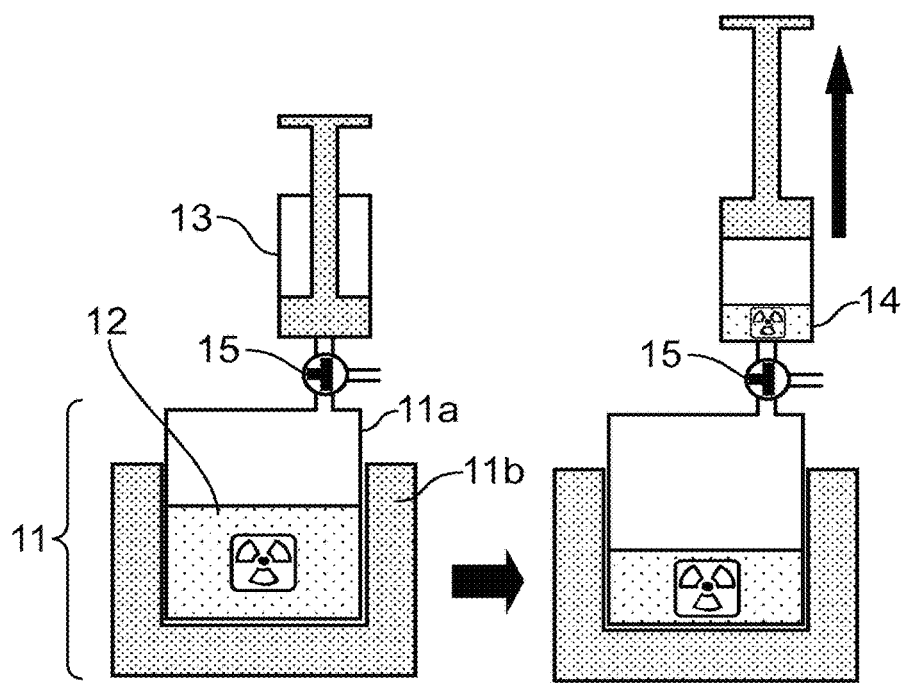
FIGS. 2A and 2B illustrate an exemplary system of the present invention.
Figure 2B:
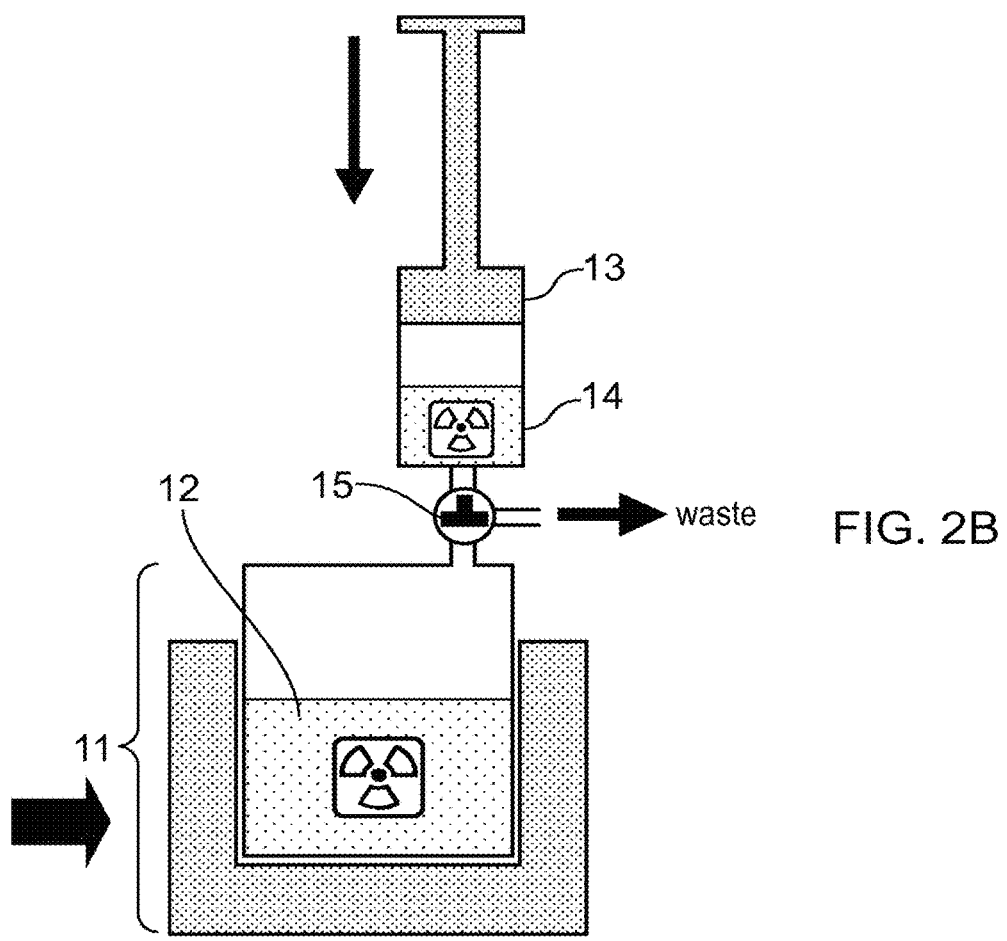
Figure 3A:
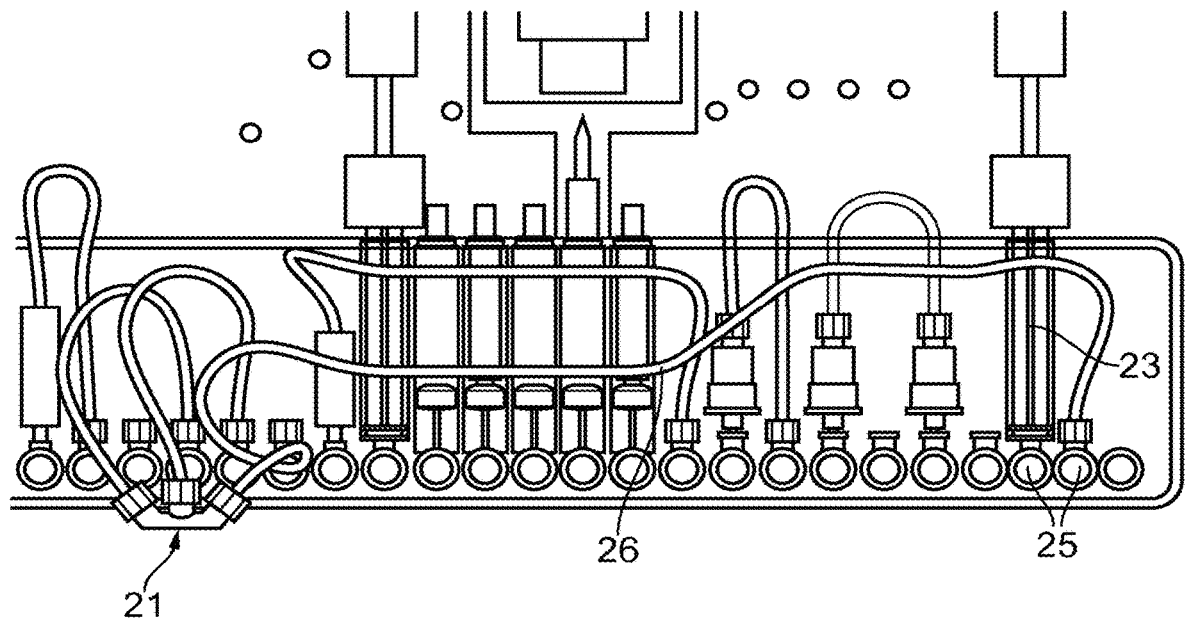
FIGS. 3A and 3B illustrate a FASTlab™ cassette for the synthesis of [$^{18}$F]FLT.
Figure 3B:
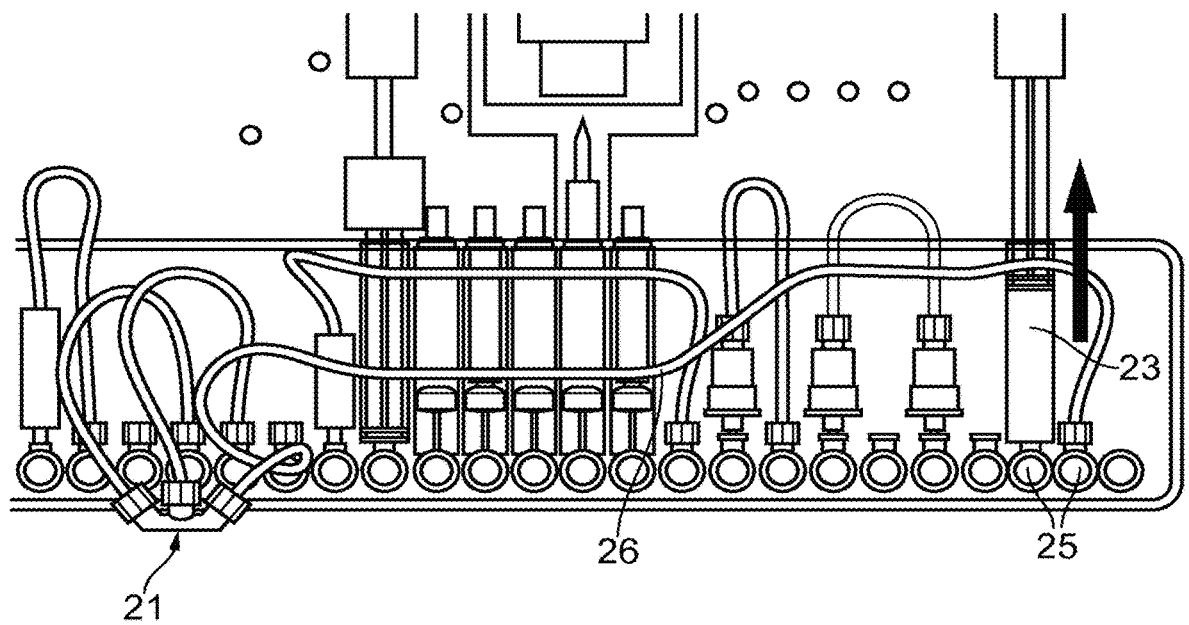

Example 1(i) describes synthesis of non-radioactive FLT using FASTlab™ to assess acetonitrile residual content.

Example 1(ii) describes synthesis of [$^{18}$F]FLT using FASTlab™ to assess the amount of volatile radioactive material generated.

LIST OF ABBREVIATIONS USED IN THE EXAMPLES

FLT fluorothymidine
sec second(s)
mBar millibar(s)
ppm parts per million

EXAMPLES

Example 1: Comparative View of Classical Vs. Inventive Evaporation Systems

Classical evaporation: 110° C., for 450 sec, −600 mBar (vacuum pump set point), N$_2$ pressure—low flow valve
Closed evaporation system: 110° C., for 450 sec, the 6 ml syringe is emptied 3 times
Example 1(i) and Example 1(ii) below both use FASTlab™ and a cassette designed for the production of FLT.
1(i) Cold Runs to Assess the Acetonitrile Residual Content

| Method | Residual acetonitrile (ppm) |
| --- | --- |
| Closed evaporation system | 2109 |
| Closed evaporation system | 1726 |
| Closed evaporation system | 2353 |
| Classical evaporation | 67030 |
| Classical evaporation | 47015 |
| Classical evaporation | 54342 |
| Closed evaporation system | 2309 |
| Closed evaporation system | 2661 |
| Classical evaporation | 97326 |
| Classical evaporation | 87924 |
| Classical evaporation | 88340 |
| Mean | |

| Method | Residual acetonitrile (ppm) |
| --- | --- |
| Classical evaporation | 73663 |
| Closed evaporation system | 2232 |

Conclusions: the closed evaporation systems results in a lower amount of acetonitrile as compared with the known evaporation method.

1(ii) Hot Runs to Assess the Activity Balance

| Method | Activity balance (%) |
| --- | --- |
| Closed evaporation system | 96.5% |
| Closed evaporation system | 96.37% |
| Closed evaporation system | 94.15% |
| Classical evaporation | 89.4% |
| Mean | |
| Classical evaporation | 89.4% |
| Closed evaporation system | 95.7% |

Conclusions: the closed evaporation system reduces the amount of volatiles generated during the drying step.

The invention claimed is:

1. A method for the automated synthesis of a radiolabelled compound within a cassette of an automated radiosynthesis apparatus wherein said method comprises:
   (i) radiolabelling a protected precursor compound in a fixed volume container of the cassette to obtain a protected radiolabelled compound;
   (ii) deprotecting the protected radiolabelled compound obtained from radiolabelling step (i) to obtain said radiolabelled compound wherein said deprotection is effected using a hydrolysis medium;
   (iii) connecting the fixed volume container via a 3-way valve to an expandable volume of the cassette, wherein said expandable volume is within a syringe and said 3-way valve has a first position and a second position; and,
   (iv) heating the radioactive fluid in the fixed volume container above its boiling point to reach the equilibrium gas/liquid phase while the 3-way valve is in the first position causing said liquid to vaporize and move into the expandable volume where it condenses due to the drop in temperature to form a volume of radioactive fluid in the expandable volume to form a condensed radioactive fluid, then positioning the 3-way valve to the second position to empty said condensed radioactive fluid to waste.

2. The method as defined in claim 1 wherein said fixed volume container is a reaction vessel.

3. The method as defined in claim 1 wherein said radiolabelled compound is a radiopharmaceutical.

4. The method as defined in claim 3 wherein said radiopharmaceutical is a diagnostic radiopharmaceutical.

5. The method as defined in claim 4 wherein said diagnostic radiopharmaceutical is either a single photon emission tomography (SPECT) tracer or a positron emission tomography (PET) tracer.

6. The method as defined in claim 5 wherein said diagnostic radiopharmaceutical is a PET tracer.

7. The method as defined in claim 6 wherein said PET tracer comprises a $^{11}$C-labelled compound or an $^{18}$F-labelled compound.

8. The method as defined in claim 7 wherein said $^{18}$F-labelled compound is selected from [$^{18}$F]fluorodeoxyglucose ([$^{18}$F]FDG), [$^{18}$F]fluorothymidine ([$^{18}$F]FLT), anti-1-amino-3-[$^{18}$F]fluorocyclobutyl-1-carboxylic acid ([$^{18}$F]FACBC), [$^{18}$F]fluoromisonidazole ([$^{18}$F]FMISO), [$^{18}$F]fluoro-L-DOPA ([$^{18}$F]DOPA), O-(-2-[$^{18}$F]fluoroethyl)-L-tyrosine ([$^{18}$F]FET), 16a-[$^{18}$F]fluoro-1 78-estradiol ([$^{18}$F]FES) and [$^{18}$F]-1-(5-fluoro-5-deoxy-a-aribinofuranosyl)-2-nitroimidazole ([$^{18}$F]-FAZA).

9. The method as defined in claim 8 wherein said $^{18}$F-labelled compound is selected from [$^{18}$F]FDG, [$^{18}$F]FLT, [$^{18}$F]FACBC and [$^{18}$F]FMISO.

10. The method as defined in claim 9 wherein said $^{18}$F-labelled compound is [$^{18}$F]FLT.

11. The method as defined in claim 1 wherein the automated radiosynthesis apparatus controls the cassette from outside the cassette.

12. The method as defined in claim 1 wherein the cassette comprises a linear array of valves each linked to a port where reagents or vials can be attached.

13. The method as defined in claim 12 wherein the port is attached to the reagents or the vials by either a needle puncture of an inverted septum, a sealed vial, or a gas-tight marrying joint.

14. The method as defined in claim 11 wherein the syringe comprises a plunger and the automated radiosynthesis apparatus controls the plunger of the syringe to expand or collapse the expandable volume of the syringe.

15. The method as defined in claim 1 wherein the cassette comprises 15 to 40 valves in a linear array.

16. A method for the automated synthesis of a radiolabelled compound within a cassette of an automated radiosynthesis apparatus wherein said method comprises:
 (i) radiolabelling a protected precursor compound in a reaction vessel of the cassette to obtain a protected radiolabelled compound;
 (ii) deprotecting the protected radiolabelled compound obtained from radiolabelling step (i) to obtain said radiolabelled compound wherein said deprotection is effected using a hydrolysis medium, wherein the hydrolysis medium is an acidic or a basic solution;
 (iii) connecting the fixed volume container via a 3-way valve to an expandable volume of the cassette and said 3-way valve has a first position and a second position, wherein said expandable volume is within a syringe and the syringe comprises a plunger whereby the automated radiosynthesis apparatus controls the plunger of the syringe to expand or collapse the expandable volume of the syringe; and,
 (iv) heating the radioactive fluid in the reaction vessel above its boiling point to reach the equilibrium gas/liquid phase while the 3-way valve is in the first position causing said liquid to vaporize and move into the expandable volume of the syringe where it condenses due to the drop in temperature to form a volume of radioactive fluid in the expandable volume of the syringe to form a condensed radioactive fluid, then positioning the 3-way valve to the second position to empty said condensed radioactive fluid to waste.

17. The method as defined in claim 16 wherein said radiolabelled compound is a radiopharmaceutical.

18. The method as defined in claim 17 wherein said radiopharmaceutical is a diagnostic radiopharmaceutical.

19. The method as defined in claim 18 wherein said diagnostic radiopharmaceutical is either a single photon emission tomography (SPECT) tracer or a positron emission tomography (PET) tracer.

20. The method as defined in claim 19 wherein said PET tracer comprises a $^{11}$C-labelled compound or an $^{18}$F-labelled compound.

* * * * *